US00PP36477P2

(12) United States Plant Patent
Heuger

(10) Patent No.: US PP36,477 P2
(45) Date of Patent: Feb. 18, 2025

(54) ***HELLEBORUS* PLANT NAMED 'HM 1218'**

(50) Latin Name: ***Helleborus ballardiae* X *Helleborus* x *hybridus***
Varietal Denomination: HM 1218

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,421

(22) Filed: Nov. 14, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

(56) References Cited

PUBLICATIONS https://zielonozakreceni-pl.translate.goog/forum/ciemierniki/11910-ciemiernik-iburgski-helleborus-x-iburgensis-hgc-ice-n-roses-mindy-marble?_x_tr_sl=pl&_x_tr_tl=en&_x_tr_hl=en&_x_tr_pto=sc Retrieved from the Internet on Mar. 21, 2024.*
Heuger.*

* cited by examiner

*Primary Examiner* — Susan McCormick Ewoldt
(74) *Attorney, Agent, or Firm* — C. Anne Whealy

(57) ABSTRACT

A new and distinct cultivar of *Helleborus* plant named 'HM 1218', characterized by its upright to somewhat outwardly spreading and mounded plant habit; moderately vigorous to vigorous growth habit; dark green-colored leaflets with lighter green-colored venation; freely flowering habit; red-colored flowers; and good garden performance.

1 Drawing Sheet

Figure 1:
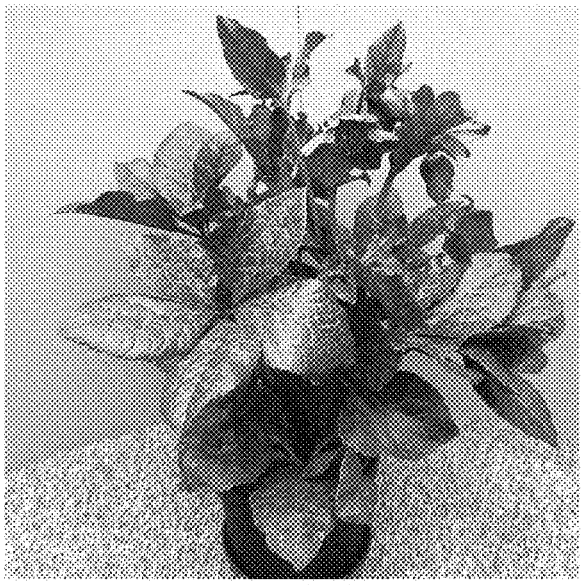

Botanical designation: *Helleborus ballardiae* X *Helleborus* x *hybridus.*
Cultivar denomination: 'HM 1218'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jan. 30, 2024, application number 2024/0243. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus ballardiae* X *Helleborus* x *hybridus* and hereinafter referred to by the name 'HM 1218'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in November 2014 of a proprietary selection of *Helleborus ballardiae* identified as code number P482, not patented, as the female, or seed, parent and a proprietary selection of *Helleborus* x *hybridus* identified as code number O1578, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December 2016.

Asexual reproduction of the new *Helleborus* plant by in vitro axillary meristem culture in a controlled environment in Glandorf, Germany since May 2017 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HM 1218'. These characteristics in combination distinguish 'HM 1218' as a new and distinct *Helleborus* plant:

1. Upright to somewhat outwardly spreading and mounded plant habit.
2. Vigorous growth habit.
3. Dark green-colored leaflets with lighter green-colored venation.

4. Freely flowering habit.
5. Red-colored flowers.
6. Good garden performance.

Plants of the new *Helleborus* differ from plants of the female parent selection in the following characteristics:

1. Leaf venation of leaflets of plants of the new *Helleborus* is more distinct than leaf venation of leaflets of plants of the female parent selection.
2. Flowers of plants of the new *Helleborus* are red in color whereas flowers of plants of the female parent selection are creamy white to pink in color.

Plants of the new *Helleborus* differ from plants of the male parent selection in the following characteristics:

1. Leaf venation of leaflets of plants of the new *Helleborus* is more distinct than leaf venation of leaflets of plants of the male parent selection.
2. Flowers of plants of the new *Helleborus* are red in color whereas flowers of plants of the male parent selection are pink in color.

Plants of the new *Helleborus* can also be compared to plants of *Helleborus* x *ericsmithii* X *Helleborus* x *hybridus* 'COSEH 4500', disclosed in U.S. Plant Pat. No. 28,293. In side-by-side comparisons, plants of the new *Helleborus* differ primarily from plants of 'COSEH 4500' in the following characteristics:

1. Leaf venation of leaflets of plants of the new *Helleborus* is more distinct than leaf venation of leaflets of plants of 'COSEH 4500'.
2. Flowers of plants of the new *Helleborus* are red in color whereas flowers of plants of 'COSEH 4500' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph at the top of the sheet (FIG. 1) is a side perspective view of a typical flowering plant of 'HM 1218' grown in a container.

Figure 2:
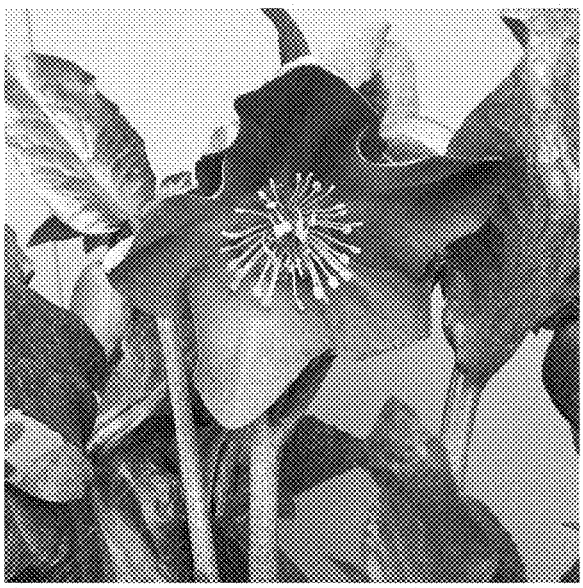

The photograph at the bottom of the sheet (FIG. 2) is a close-up view of a typical flowering plant of 'HM 1218'.

DETAILED BOTANICAL DESCRIPTION

The aforementioned photographs and following observations, measurements and values describe plants grown during the early spring in 15-cm containers in a glass-covered greenhouse in Glandorf, Germany and under cultural practices typical of commercial *Helleborus* production. During the production of the plants, day temperatures ranged from 12 C to 25 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus ballardiae* X *Helleborus* x *hybridus* 'HM 1218'.

Parentage:

*Female, or seed, parent*.—Proprietary selection of *Helleborus ballardiae* identified as code number P482, not patented.

*Male, or pollen, parent*.—Proprietary selection of *Helleborus* x *hybridus* identified as code number O1578, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held above the foliar plane; plant shape, roughly globular; vigorous growth habit and moderate to rapid growth rate.

*Plant height, soil level to top of foliar plane*.—About 25.6 cm.

*Plant height, soil level to top of flowers*.—About 51.8 cm.

*Plant diameter* (*area of spread*).—About 73.5 cm.

Leaf description:

*Arrangement*.—Leaves arranged in a basal rosette; leaves palmately compound with typically three to five leaflets per leaf.

*Leaf length*.—About 17 cm.

*Leaf width*.—About 22.6 cm.

*Leaflet length*.—About 12.1 cm.

*Leaflet width*.—About 7.1 cm.

*Leaf shape*.—Palmate; roughly reinform in outline.

*Leaflet shape*.—Elliptic to ovate.

*Leaflet apex*.—Acute.

*Leaflet base*.—Attenuate.

*Leaflet margin*.—Serrate; slightly coarsely undulate.

*Leaflet texture and luster, upper and lower surfaces*.—Smooth, glabrous; coriaceous and tough; slightly to moderately glossy.

*Leaflet venation pattern*.—Pinnate and reticulate.

*Leaflet color*.—Developing leaflets, upper surface: Close to NN137A; venation, close to 144B; midvein, tinged proximally with close to 178A. Developing leaflets, lower surface: Slightly darker than 147B; venation, close to 187A. Fully developed leaflets, upper surface: Darker than a blend of 139A and 147A; venation, close to 143B, proximally, tinged with close to 200B. Fully developed leaflets, lower surface: Slightly darker than a blend of 147B and 148A and slightly to moderately tinged with close to N186C; venation, close to N186C.

*Petioles*.—Length: About 21.4 cm. Diameter: About 5 mm by 5.5 mm. Strength: Strong. Texture and luster, upper and lower surfaces: Smooth, glabrous; moderately glossy. Color, upper and lower surfaces: Close to 146B; heavily covered with fine dots, close to 177A.

Flower description:

*Flower shape and habit*.—Single rotate bowl-shaped flowers arranged in panicles; freely flowering habit with about eight to twelve flowers per inflorescence and about 110 flowers and flower buds per plant; flowers face mostly outwardly to slightly nodding.

*Fragrance*.—None detected.

*Natural flowering season*.—Plants begin flowering about ten months after planting; plants flower naturally from late winter into early spring in Germany.

*Flower longevity on the plant*.—About ten days; sepals persistent, other flower parts are not persistent.

*Flower buds*.—Length: About 2.3 cm. Diameter: About 1.3 cm. Shape: Ovate to oblong. Texture and luster: Smooth, glabrous; slightly glossy. Color: Close to 182B; towards the apex, close to 183D.

*Inflorescence height* (*including peduncle*).—About 48.5 cm.

*Inflorescence diameter*.—About 22.3 cm.

*Flower diameter*.—About 6.6 cm.

*Flower depth*.—About 2.7 cm.

*Petals*.—All petals are transformed into nectaries.

*Sepals*.—Quantity and arrangement: About five, arranged in a single whorl. Length: About 3.6 cm. Width: About 2.8 cm. Shape: Broadly ovate; slightly to moderately concave. Apex: Broadly and bluntly acute. Base: Truncate to rounded. Margin: Entire. Texture and luster, upper surface: Smooth, glabrous; matte to slightly glossy. Texture and luster, lower surface: Smooth, glabrous; slightly glossy. Color: When opening, upper surface: Close to 183D; center, close to 182B; towards the base, close to 146D. When opening, lower surface: Close to 183C to 183D; venation, close to 183B. Fully opened, upper surface: Close to 184B and 185B; towards the base, close to 146D; venation, similar to lamina colors; color does not change with subsequent development. Fully opened, lower surface: Close to 184B; center, close to 185D; venation, similar to lamina colors; color does not change with subsequent development.

*Flower bracts*.—Quantity per flower: Typically one or two. Length: About 7.3 cm. Width: About 4.2 cm. Shape: Broadly obovate to broadly ovate. Apex: Acute to three-parted with acute tips. Base: Truncate to cuneate. Margin: Proximally, entire; distally, finely serrate; slightly coarsely undulate. Color, upper surface: Close to NN137A; towards the base, slightly tinged with close to 178A to 178B; venation, close to 144A. Color, lower surface: Darker than 148A tinged with close to N186C.

*Peduncles*.—Length: About 40.5 cm. Diameter: About 7 mm to 8 mm. Aspect: About 20 degrees from vertical. Strength: Strong. Texture and luster: Smooth, glabrous; moderately glossy. Color: Close to 146D; heavily covered with fine dots, close to 183D.

*Pedicels*.—Length: About 1.9 cm. Diameter: About 2 mm. Aspect: About 10 to 45 degrees from peduncle axis. Strength: Moderately strong. Texture and luster: Smooth, glabrous; moderately glossy. Color: Close to 178A; moderately covered with fine dots, close to 146D to lighter than 146D.

*Reproductive organs*.—Stamens: Quantity per flower: About 80. Filament length: About 1.6 cm. Filament color: Close to 155A. Anther shape: Double and broadly reniform; basifixed. Anther size: About 2 mm by 2.5 mm. Anther color: Close to 150C. Pollen amount: Sparse. Pollen color: Close to 4D to lighter than 4D. Pistils: Quantity per flower: About four to eight. Pistil length: About 1.5 cm. Stigma diameter: About 0.3 mm. Stigma shape: Club-shaped. Stigma color: Close to 155D. Style length: About 1.45 cm. Style color: Close to 185B. Ovary color: Close to 176B. Nectaries (transformed petals): Quantity per flower: About 13. Length: About 1.1 cm. Diameter: About 3.5 mm. Shape: Tubular, flattened; apices, obtuse. Texture and luster, inner and outer surfaces: Smooth, glabrous; slightly glossy. Color, immature, inner and outer surfaces: Close to N144A; towards the apex, close to N144B. Color, mature, inner surface: Proximally, close to N144A; distally, close to N170A; venation, similar to lamina colors; with subsequent development, proximally, color becoming closer to 153B and distally, close to 166B. Color, mature, outer surface: Proximally, close to N144A; distally, close to N170A; at the base, close to 146D; venation, similar to lamina colors; with subsequent development, proximally, color becoming closer to 153B and distally, close to 166B, and at the base, close to 152D.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HM 1218' as illustrated and described.

* * * * *